United States Patent
Gannoe et al.

(10) Patent No.: US 7,211,094 B2
(45) Date of Patent: *May 1, 2007

(54) MAGNETIC ANCHORING DEVICES

(75) Inventors: Jamy Gannoe, Redwood City, CA (US); Craig Gerbi, Mountain View, CA (US)

(73) Assignee: Satiety, Inc., Palo Alto, CA (US)

( * ) Notice: Subject to any disclaimer, the term of this patent is extended or adjusted under 35 U.S.C. 154(b) by 396 days.

This patent is subject to a terminal disclaimer.

(21) Appl. No.: 10/689,774

(22) Filed: Oct. 20, 2003

(65) Prior Publication Data

US 2004/0088008 A1    May 6, 2004

Related U.S. Application Data

(63) Continuation of application No. 10/288,820, filed on Nov. 5, 2002, now Pat. No. 6,656,194.

(51) Int. Cl.
*A61B 17/08* (2006.01)
(52) U.S. Cl. .................................... 606/151
(58) Field of Classification Search ............... 606/151, 606/153, 157, 213, 214; 607/72, 73, 116, 607/40, 133
See application file for complete search history.

(56) References Cited

U.S. PATENT DOCUMENTS

| | | |
|---|---|---|
| 2,108,206 A | 2/1938 | Meeker |
| 2,508,690 A | 5/1950 | Schmerl |
| 3,372,443 A | 3/1968 | Daddonna, Jr. |
| 3,395,710 A | 8/1968 | Stratton et al. |
| 3,986,493 A | 10/1976 | Hendren, III |
| 4,057,065 A | 11/1977 | Thow |
| 4,063,561 A | 12/1977 | McKenna et al. |
| 4,133,315 A | 1/1979 | Berman et al. |
| 4,134,405 A | 1/1979 | Smit |
| 4,198,982 A | 4/1980 | Fortner et al. |
| 4,246,893 A | 1/1981 | Berson |

(Continued)

FOREIGN PATENT DOCUMENTS

EP    0 137 878 A1    4/1985

(Continued)

OTHER PUBLICATIONS

U.S. Appl. No. 10/288,820, filed Nov. 5, 2002 Gannoe et al.

(Continued)

*Primary Examiner*—Kevin T. Truong
(74) *Attorney, Agent, or Firm*—Fulwider Patton LLP

(57) ABSTRACT

Magnetic anchoring devices are disclosed herein. Expandable devices that are inserted into the stomach of a patient are attached to its interior wall by magnetically coupling. Such expandable devices, like inflatable balloons, comprise at least one magnetic device, which may be a magnet, a magnetizable material, or a magnetic metal. The magnetic device may be positioned on the external or interior surface of the expandable device or may be integral thereto. The magnetic device is magnetically coupled to a magnetic anchor positioned on a surface of the stomach wall. In this way, the expandable devices are anchored to the stomach walls, preventing migration of the device to other areas of the body where they may become obstructions and pose health risks.

9 Claims, 10 Drawing Sheets

U.S. PATENT DOCUMENTS

| | | |
|---|---|---|
| 4,258,705 A | 3/1981 | Sorensen et al. |
| 4,315,509 A | 2/1982 | Smit |
| 4,343,066 A | 8/1982 | Lance |
| 4,402,445 A | 9/1983 | Green |
| 4,416,267 A | 11/1983 | Garren et al. |
| 4,458,681 A | 7/1984 | Hopkins |
| 4,485,805 A | 12/1984 | Foster, Jr. |
| 4,501,264 A | 2/1985 | Rockey |
| 4,547,192 A | 10/1985 | Brodsky et al. |
| 4,558,699 A | 12/1985 | Bashour |
| 4,592,339 A | 6/1986 | Kuzmak et al. |
| 4,592,354 A | 6/1986 | Rothfuss |
| 4,598,699 A | 7/1986 | Garren et al. |
| 4,607,618 A | 8/1986 | Angelchik |
| 4,610,383 A | 9/1986 | Rothfuss et al. |
| 4,636,205 A | 1/1987 | Steer |
| 4,641,653 A | 2/1987 | Rockey |
| 4,643,169 A | 2/1987 | Koss et al. |
| 4,646,722 A | 3/1987 | Silverstein et al. |
| 4,648,383 A | 3/1987 | Angelchik |
| 4,671,287 A | 6/1987 | Fiddian-Green |
| 4,694,827 A | 9/1987 | Weiner et al. |
| 4,716,900 A | 1/1988 | Ravo et al. |
| 4,723,547 A | 2/1988 | Kullas et al. |
| 4,739,758 A | 4/1988 | Lai et al. |
| 4,744,363 A | 5/1988 | Hasson |
| 4,773,393 A | 9/1988 | Haber et al. |
| 4,790,294 A | 12/1988 | Allred, III et al. |
| 4,803,985 A | 2/1989 | Hill |
| 4,841,888 A | 6/1989 | Mills et al. |
| 4,899,747 A | 2/1990 | Garren et al. |
| 4,905,693 A | 3/1990 | Ravo |
| 4,925,446 A | 5/1990 | Garay et al. |
| 4,927,428 A | 5/1990 | Richards |
| 4,969,474 A | 11/1990 | Schwarz |
| 5,037,021 A | 8/1991 | Mills et al. |
| 5,059,193 A | 10/1991 | Kuslich |
| 5,080,663 A | 1/1992 | Mills et al. |
| 5,084,061 A | 1/1992 | Gau et al. |
| 5,112,310 A | 5/1992 | Grobe |
| 5,129,915 A | 7/1992 | Cantenys |
| 5,146,933 A | 9/1992 | Boyd |
| 5,156,609 A | 10/1992 | Nakao et al. |
| 5,171,233 A | 12/1992 | Amplatz et al. |
| 5,197,649 A | 3/1993 | Bessler et al. |
| 5,220,928 A | 6/1993 | Oddsen et al. |
| 5,222,961 A | 6/1993 | Nakao et al. |
| 5,226,429 A | 7/1993 | Kuzmak |
| 5,234,454 A | 8/1993 | Bangs |
| 5,246,456 A | 9/1993 | Wilkinson |
| 5,250,058 A | 10/1993 | Miller et al. |
| 5,254,126 A | 10/1993 | Filipi et al. |
| 5,259,366 A | 11/1993 | Reydel et al. |
| 5,259,399 A | 11/1993 | Brown |
| 5,261,920 A | 11/1993 | Main et al. |
| 5,263,629 A | 11/1993 | Trumbull et al. |
| 5,297,536 A | 3/1994 | Wilk |
| 5,301,658 A | 4/1994 | Zhu et al. |
| 5,306,300 A | 4/1994 | Berry |
| 5,309,896 A | 5/1994 | Moll et al. |
| 5,309,927 A | 5/1994 | Welch |
| 5,327,914 A | 7/1994 | Shlain |
| 5,330,486 A | 7/1994 | Wilk |
| 5,330,503 A | 7/1994 | Yoon |
| 5,331,975 A | 7/1994 | Bonutti |
| 5,334,209 A | 8/1994 | Yoon |
| 5,334,210 A | 8/1994 | Gianturco |
| 5,345,949 A | 9/1994 | Shlain |
| 5,346,501 A | 9/1994 | Regula et al. |
| 5,355,897 A | 10/1994 | Pietrafitta et al. |
| 5,376,095 A | 12/1994 | Ortiz |
| 5,382,231 A | 1/1995 | Shlain |
| 5,403,312 A | 4/1995 | Yates et al. |
| 5,403,326 A | 4/1995 | Harrison et al. |
| 5,411,508 A | 5/1995 | Bessler et al. |
| 5,433,721 A | 7/1995 | Hooven et al. |
| 5,437,291 A | 8/1995 | Pasricha et al. |
| 5,449,368 A | 9/1995 | Kuzmak |
| 5,452,837 A | 9/1995 | Williamson, IV et al. |
| 5,458,131 A | 10/1995 | Wilk |
| 5,465,894 A | 11/1995 | Clark et al. |
| 5,467,911 A | 11/1995 | Tsuruta et al. |
| 5,486,183 A | 1/1996 | Middleman et al. |
| 5,489,058 A | 2/1996 | Plyley et al. |
| 5,503,635 A | 4/1996 | Sauer et al. |
| 5,527,319 A | 6/1996 | Green et al. |
| 5,535,935 A | 7/1996 | Vidal et al. |
| 5,542,949 A | 8/1996 | Yoon |
| 5,549,621 A | 8/1996 | Bessler et al. |
| 5,551,622 A | 9/1996 | Yoon |
| 5,555,898 A | 9/1996 | Suzuki et al. |
| 5,558,665 A | 9/1996 | Kieturakis |
| 5,571,116 A | 11/1996 | Bolanos et al. |
| 5,577,654 A | 11/1996 | Bishop |
| 5,578,044 A | 11/1996 | Gordon et al. |
| 5,582,616 A | 12/1996 | Bolduc et al. |
| 5,584,861 A | 12/1996 | Swain et al. |
| 5,588,579 A | 12/1996 | Schnut et al. |
| 5,601,604 A | 2/1997 | Vincent |
| 5,603,443 A | 2/1997 | Clark et al. |
| 5,607,094 A | 3/1997 | Clark et al. |
| 5,624,381 A | 4/1997 | Kieturakis |
| 5,626,588 A | 5/1997 | Sauer et al. |
| 5,639,008 A | 6/1997 | Gallagher et al. |
| 5,649,937 A | 7/1997 | Bito et al. |
| 5,651,769 A | 7/1997 | Waxman et al. |
| 5,655,698 A | 8/1997 | Yoon |
| 5,662,664 A | 9/1997 | Gordon et al. |
| 5,662,667 A | 9/1997 | Knodel |
| 5,667,520 A | 9/1997 | Bonutti |
| 5,676,659 A | 10/1997 | McGurk |
| 5,676,674 A | 10/1997 | Bolanos et al. |
| 5,685,868 A | 11/1997 | Lundquist |
| 5,690,656 A | 11/1997 | Cope |
| 5,697,943 A | 12/1997 | Sauer et al. |
| 5,707,382 A | 1/1998 | Sierocuk et al. |
| 5,722,990 A | 3/1998 | Sugarbaker et al. |
| 5,728,178 A | 3/1998 | Buffington et al. |
| 5,735,848 A | 4/1998 | Yates et al. |
| 5,749,893 A | 5/1998 | Vidal et al. |
| 5,755,730 A | 5/1998 | Swain et al. |
| 5,766,216 A | 6/1998 | Gangal et al. |
| 5,776,054 A | 7/1998 | Bobra |
| 5,782,844 A | 7/1998 | Yoon et al. |
| 5,788,715 A | 8/1998 | Watson, Jr. et al. |
| 5,792,153 A | 8/1998 | Swain et al. |
| 5,797,931 A | 8/1998 | Bito et al. |
| 5,810,851 A | 9/1998 | Yoon |
| 5,810,855 A | 9/1998 | Rayburn et al. |
| 5,810,882 A | 9/1998 | Bolduc et al. |
| 5,816,471 A | 10/1998 | Plyley et al. |
| 5,820,584 A | 10/1998 | Crabb |
| 5,824,008 A | 10/1998 | Bolduc et al. |
| 5,827,298 A | 10/1998 | Hart et al. |
| 5,833,690 A | 11/1998 | Yates et al. |
| 5,836,311 A | 11/1998 | Borst et al. |
| 5,839,639 A | 11/1998 | Sauer et al. |
| 5,860,581 A | 1/1999 | Robertson et al. |
| 5,861,036 A | 1/1999 | Godin |
| 5,868,141 A | 2/1999 | Ellias |
| 5,868,760 A | 2/1999 | McGuckin, Jr. |
| 5,876,448 A | 3/1999 | Thompson et al. |
| 5,879,371 A | 3/1999 | Gardiner et al. |
| 5,887,594 A | 3/1999 | LoCicero, III |

| | | |
|---|---|---|
| 5,888,196 A | 3/1999 | Bonutti |
| 5,897,534 A | 4/1999 | Heim et al. |
| 5,897,562 A | 4/1999 | Bolanos et al. |
| 5,904,147 A | 5/1999 | Conlan et al. |
| 5,906,625 A | 5/1999 | Bito et al. |
| 5,910,105 A | 6/1999 | Swain et al. |
| 5,910,149 A | 6/1999 | Kuzmak |
| 5,921,993 A | 7/1999 | Yoon |
| 5,927,284 A | 7/1999 | Borst et al. |
| 5,928,264 A | 7/1999 | Sugarbaker et al. |
| 5,935,107 A | 8/1999 | Taylor et al. |
| 5,938,669 A | 8/1999 | Klaiber et al. |
| 5,947,983 A | 9/1999 | Solar et al. |
| 5,964,772 A | 10/1999 | Bolduc et al. |
| 5,964,782 A | 10/1999 | Lafontaine et al. |
| 5,972,001 A | 10/1999 | Yoon |
| 5,972,002 A | 10/1999 | Bark et al. |
| 5,976,161 A | 11/1999 | Kirsch et al. |
| 5,980,537 A | 11/1999 | Ouchi |
| 5,993,464 A | 11/1999 | Knodel |
| 5,993,473 A | 11/1999 | Chan et al. |
| 6,015,378 A | 1/2000 | Borst et al. |
| 6,030,364 A | 2/2000 | Durgin et al. |
| 6,030,392 A | 2/2000 | Dakov |
| 6,042,538 A | 3/2000 | Puskas |
| 6,044,847 A | 4/2000 | Carter et al. |
| 6,067,991 A | 5/2000 | Forsell |
| 6,074,343 A | 6/2000 | Nathanson et al. |
| 6,083,241 A | 7/2000 | Longo et al. |
| 6,086,600 A | 7/2000 | Kortenbach |
| 6,113,609 A | 9/2000 | Adams |
| 6,119,913 A | 9/2000 | Adams et al. |
| 6,120,513 A | 9/2000 | Bailey et al. |
| 6,136,006 A | 10/2000 | Johnson et al. |
| 6,159,146 A | 12/2000 | El Gazayerli |
| 6,159,195 A | 12/2000 | Ha et al. |
| 6,165,183 A | 12/2000 | Kuehn et al. |
| 6,179,195 B1 | 1/2001 | Adams et al. |
| 6,186,942 B1 | 2/2001 | Sullivan et al. |
| 6,186,985 B1 | 2/2001 | Snow |
| 6,179,022 B1 | 3/2001 | Baker |
| 6,197,022 B1 | 3/2001 | Baker |
| 6,200,318 B1 | 3/2001 | Har-Shai et al. |
| 6,206,822 B1 | 3/2001 | Foley et al. |
| 6,206,893 B1 | 3/2001 | Klein et al. |
| 6,224,614 B1 | 5/2001 | Yoon |
| 6,231,561 B1 | 5/2001 | Frazier et al. |
| 6,248,058 B1 | 6/2001 | Silverman et al. |
| 6,254,642 B1 | 7/2001 | Taylor |
| 6,273,897 B1 | 8/2001 | Dalessandro et al. |
| 6,279,809 B1 | 8/2001 | Nicolo |
| 6,290,674 B1 | 9/2001 | Roue et al. |
| 6,293,923 B1 | 9/2001 | Yachia et al. |
| 6,302,917 B1 | 10/2001 | Dua et al. |
| 6,312,437 B1 | 11/2001 | Kortenbach |
| 6,328,689 B1 | 12/2001 | Gonzalez et al. |
| 6,338,345 B1 | 1/2002 | Johnson et al. |
| 6,352,543 B1 | 3/2002 | Cole |
| 6,358,197 B1 | 3/2002 | Silverman et al. |
| 6,379,366 B1 | 4/2002 | Fleischman et al. |
| 6,387,104 B1 | 5/2002 | Pugsley, Jr. et al. |
| 6,398,795 B1 | 6/2002 | McAlister et al. |
| 6,416,535 B1 | 7/2002 | Lazarus |
| 6,423,087 B1 | 7/2002 | Sawada |
| 6,432,040 B1 | 8/2002 | Meah |
| 6,447,533 B1 | 9/2002 | Adams |
| 6,460,543 B1 | 10/2002 | Forsell |
| 6,475,136 B1 | 11/2002 | Forsell |
| 6,491,707 B2 | 12/2002 | Makower et al. |
| 6,494,888 B1 | 12/2002 | Laufer et al. |
| 6,506,196 B1 | 1/2003 | Laufer |
| 6,535,764 B2 | 3/2003 | Imran et al. |
| 6,540,789 B1 | 4/2003 | Silverman et al. |
| 6,551,310 B1 | 4/2003 | Ganz et al. |
| 6,554,844 B2 | 4/2003 | Lee et al. |
| 6,558,400 B2 * | 5/2003 | Deem et al. ............... 606/151 |
| 6,561,969 B2 | 5/2003 | Frazier et al. |
| 6,572,629 B2 | 6/2003 | Kalloo et al. |
| 6,592,596 B1 | 7/2003 | Geitz |
| 6,626,899 B2 | 9/2003 | Houser et al. |
| 6,632,227 B2 | 10/2003 | Adams |
| 6,663,598 B1 | 12/2003 | Carrillo, Jr. et al. |
| 6,663,639 B1 | 12/2003 | Laufer et al. |
| 6,663,640 B2 | 12/2003 | Kortenbach |
| 6,675,809 B2 | 1/2004 | Stack et al. |
| 6,682,520 B2 | 1/2004 | Ingenito |
| 6,689,062 B1 | 2/2004 | Mesallum |
| 6,692,485 B1 | 2/2004 | Brock et al. |
| 6,716,222 B2 | 4/2004 | McAlister et al. |
| 6,733,512 B2 | 5/2004 | McGhan |
| 6,736,822 B2 | 5/2004 | McClellan et al. |
| 6,740,098 B2 | 5/2004 | Abrams et al. |
| 6,740,121 B2 | 5/2004 | Geitz |
| 6,746,489 B2 | 6/2004 | Dua et al. |
| 6,754,536 B2 | 6/2004 | Swoyer et al. |
| 6,755,849 B1 | 6/2004 | Gowda et al. |
| 6,755,869 B2 | 6/2004 | Geitz |
| 6,756,364 B2 | 6/2004 | Barbier et al. |
| 6,764,518 B2 | 7/2004 | Godin |
| 6,773,440 B2 | 8/2004 | Gannoe et al. |
| 6,773,441 B1 | 8/2004 | Laufer |
| 6,786,898 B2 | 9/2004 | Guenst |
| 6,790,214 B2 | 9/2004 | Kraemer et al. |
| 6,802,868 B2 | 10/2004 | Silverman et al. |
| 6,821,285 B2 | 11/2004 | Laufer et al. |
| 6,835,199 B2 | 12/2004 | McGuckin, Jr. et al. |
| 6,835,200 B2 | 12/2004 | Laufer et al. |
| 6,837,848 B2 | 1/2005 | Bonner et al. |
| 6,840,423 B2 | 1/2005 | Adams et al. |
| 6,845,776 B2 | 1/2005 | Stack et al. |
| 6,896,682 B1 | 5/2005 | McClellan et al. |
| 6,926,722 B2 | 8/2005 | Geitz |
| 6,966,919 B2 | 11/2005 | Sixto, Jr. et al. |
| 6,981,978 B2 | 1/2006 | Gannoe |
| 6,991,643 B2 | 1/2006 | Saadat |
| 7,020,531 B1 * | 3/2006 | Colliou et al. ............... 607/133 |
| 7,025,791 B2 | 4/2006 | Levine et al. |
| 7,033,378 B2 | 4/2006 | Smith et al. |
| 7,037,343 B2 | 5/2006 | Imran |
| 7,037,344 B2 | 5/2006 | Kagan et al. |
| 7,063,715 B2 | 6/2006 | Onuki et al. |
| 7,083,630 B2 | 8/2006 | DeVries et al. |
| 7,087,011 B2 | 8/2006 | Cabiri et al. |
| 2001/0014800 A1 | 8/2001 | Frazier et al. |
| 2001/0020190 A1 | 9/2001 | Taylor |
| 2001/0037127 A1 | 11/2001 | De Hoyos Garza |
| 2002/0022851 A1 | 2/2002 | Kalloo et al. |
| 2002/0035361 A1 | 3/2002 | Houser et al. |
| 2002/0040226 A1 | 4/2002 | Laufer et al. |
| 2002/0047036 A1 | 4/2002 | Sullivan et al. |
| 2002/0058967 A1 | 5/2002 | Jervis |
| 2002/0072761 A1 | 6/2002 | Abrams et al. |
| 2002/0077661 A1 | 6/2002 | Saadat |
| 2002/0078967 A1 | 6/2002 | Sixto, Jr. et al. |
| 2002/0082621 A1 | 6/2002 | Schurr et al. |
| 2002/0143346 A1 | 10/2002 | McGuckin, Jr. et al. |
| 2002/0143347 A1 | 10/2002 | Cole et al. |
| 2002/0165589 A1 | 11/2002 | Imran et al. |
| 2002/0183768 A1 | 12/2002 | Deem et al. |
| 2002/0193816 A1 | 12/2002 | Laufer et al. |
| 2003/0040804 A1 | 2/2003 | Stack et al. |
| 2003/0040808 A1 | 2/2003 | Stack et al. |
| 2003/0065340 A1 | 4/2003 | Geitz |
| 2003/0065359 A1 | 4/2003 | Weller et al. |
| 2003/0093117 A1 | 5/2003 | Saadat |
| 2003/0109892 A1 | 6/2003 | Deem et al. |

| | | | | | | |
|---|---|---|---|---|---|---|
| 2003/0109931 A1 | 6/2003 | Geitz | | 2005/0198476 A1 | 9/2005 | Gazsi et al. |
| 2003/0109935 A1 | 6/2003 | Geitz | | 2005/0203548 A1 | 9/2005 | Weller et al. |
| 2003/0120265 A1 | 6/2003 | Deem et al. | | 2005/0228415 A1 | 10/2005 | Gertner |
| 2003/0120285 A1 | 6/2003 | Kortenbach | | 2005/0256587 A1 | 11/2005 | Egan |
| 2003/0120289 A1 | 6/2003 | McGuckin, Jr. et al. | | 2006/0020247 A1 | 1/2006 | Kagan et al. |
| 2003/0132267 A1 | 7/2003 | Adams et al. | | 2006/0020254 A1 | 1/2006 | Hoffmann |
| 2003/0158563 A1 | 8/2003 | McClellan et al. | | 2006/0020276 A1 | 1/2006 | Saadat et al. |
| 2003/0158601 A1 | 8/2003 | Silverman et al. | | 2006/0036267 A1 | 2/2006 | Saadat et al. |
| 2003/0171760 A1 | 9/2003 | Gambale | | | | |
| 2003/0208209 A1 | 11/2003 | Gambale et al. | | | | |
| 2003/0225312 A1 | 12/2003 | Suzuki et al. | | | | |

FOREIGN PATENT DOCUMENTS

| | | |
|---|---|---|
| EP | 0 174 843 A1 | 3/1986 |
| EP | 0 246 999 A1 | 11/1987 |
| EP | 0 540 010 A2 | 5/1993 |
| JP | 63277063 A | 11/1988 |
| JP | 63279854 | 11/1988 |
| JP | 63302863 A | 12/1988 |
| JP | 01049572 A2 | 2/1989 |
| JP | 04297219 | 10/1992 |
| WO | WO 1994/18893 A1 | 9/1994 |
| WO | WO 1999/17662 A1 | 4/1999 |
| WO | WO 1999/53827 A1 | 10/1999 |
| WO | WO 2000/32137 A1 | 6/2000 |
| WO | WO 2000/48656 A1 | 8/2000 |
| WO | WO 2000/78227 A1 | 12/2000 |
| WO | WO 2000/78229 A1 | 12/2000 |
| WO | WO 2001/66018 A1 | 9/2001 |
| WO | WO 2001/67964 A2 | 9/2001 |
| WO | WO 2001/85034 A1 | 11/2001 |
| WO | WO 2002/24080 A2 | 3/2002 |
| WO | WO 2002/35980 A2 | 5/2002 |
| WO | WO 2002/039880 A2 | 5/2002 |
| WO | WO 2002/071951 A1 | 9/2002 |
| WO | WO 2002/091961 A1 | 11/2002 |
| WO | WO 2002/096327 A2 | 12/2002 |
| WO | WO 2003/007796 A2 | 1/2003 |
| WO | WO 2003/017882 A2 | 3/2003 |
| WO | WO 2003/078721 A2 | 9/2003 |
| WO | WO 2003/086247 A1 | 10/2003 |
| WO | WO 2003/088844 A1 | 10/2003 |
| WO | WO 2003/094785 A1 | 11/2003 |
| WO | WO 2003/099140 A1 | 12/2003 |
| WO | WO 2003/105563 A2 | 12/2003 |
| WO | WO 2003/105671 A2 | 12/2003 |
| WO | WO 2004/009269 A2 | 1/2004 |
| WO | WO 2004/014237 A1 | 2/2004 |
| WO | WO 2004/017863 A2 | 3/2004 |
| WO | WO 2004/019787 A2 | 3/2004 |
| WO | WO 2004/019826 A1 | 3/2004 |
| WO | WO 2004/037064 A2 | 5/2004 |
| WO | WO 2004/049911 A2 | 6/2004 |
| WO | WO 2004/058102 A2 | 7/2004 |
| WO | WO 2004/060150 A1 | 7/2004 |
| WO | WO 2004/087014 A2 | 10/2004 |
| WO | WO 2004/103189 A1 | 12/2004 |
| WO | WO 2005/023118 A1 | 3/2005 |
| WO | WO 2005/037152 A1 | 4/2005 |
| WO | WO 2005/058239 A2 | 6/2005 |
| WO | WO 2005/060882 A1 | 7/2005 |
| WO | WO 2006/078781 A1 | 7/2006 |

| | | |
|---|---|---|
| 2004/0006351 A1 | 1/2004 | Gannoe et al. |
| 2004/0009224 A1 | 1/2004 | Miller |
| 2004/0010271 A1 | 1/2004 | Kortenbach |
| 2004/0024386 A1 | 2/2004 | Deem et al. |
| 2004/0037865 A1 | 2/2004 | Miller |
| 2004/0039452 A1 | 2/2004 | Bessler |
| 2004/0049209 A1 | 3/2004 | Benchetrit |
| 2004/0059349 A1 | 3/2004 | Sixto, Jr. et al. |
| 2004/0059354 A1 | 3/2004 | Smith et al. |
| 2004/0059358 A1 | 3/2004 | Kortenbach et al. |
| 2004/0082963 A1 | 4/2004 | Gannoe et al. |
| 2004/0087977 A1 | 5/2004 | Nolan et al. |
| 2004/0089313 A1 | 5/2004 | Utley et al. |
| 2004/0092892 A1 | 5/2004 | Kagan et al. |
| 2004/0097989 A1 | 5/2004 | Molina Trigueros |
| 2004/0107004 A1 | 6/2004 | Levine et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0122526 A1 | 6/2004 | Imran |
| 2004/0133147 A1 | 7/2004 | Woo |
| 2004/0133238 A1 | 7/2004 | Cerier |
| 2004/0138525 A1 | 7/2004 | Saadat |
| 2004/0138526 A1 | 7/2004 | Guenst |
| 2004/0138529 A1 | 7/2004 | Wiltshire et al. |
| 2004/0138531 A1 | 7/2004 | Bonner et al. |
| 2004/0138682 A1 | 7/2004 | Onuki et al. |
| 2004/0147958 A1 | 7/2004 | Lam et al. |
| 2004/0148021 A1 | 7/2004 | Cartledge et al. |
| 2004/0148034 A1 | 7/2004 | Kagan et al. |
| 2004/0158331 A1 | 8/2004 | Stack et al. |
| 2004/0162568 A1 | 8/2004 | Saadat et al. |
| 2004/0167546 A1 | 8/2004 | Saadat et al. |
| 2004/0172141 A1 | 9/2004 | Stack et al. |
| 2004/0181242 A1 | 9/2004 | Stack et al. |
| 2004/0193190 A1 | 9/2004 | Liddicoat et al. |
| 2004/0225183 A1 | 11/2004 | Michlitsch et al. |
| 2004/0225194 A1 | 11/2004 | Smith et al. |
| 2004/0225305 A1 | 11/2004 | Ewers et al. |
| 2005/0049718 A1 | 3/2005 | Dann et al. |
| 2005/0055038 A1 | 3/2005 | Kelleher et al. |
| 2005/0055039 A1 | 3/2005 | Burnett et al. |
| 2005/0075622 A1 | 4/2005 | Levine et al. |
| 2005/0075653 A1 | 4/2005 | Saadat et al. |
| 2005/0080444 A1 | 4/2005 | Kraemer et al. |
| 2005/0085787 A1 | 4/2005 | Laufer |
| 2005/0096750 A1 | 5/2005 | Kagan et al. |
| 2005/0119671 A1 | 6/2005 | Reydel et al. |
| 2005/0143760 A1 | 6/2005 | Imran |
| 2005/0148818 A1 | 7/2005 | Mesallum |
| 2005/0149067 A1 | 7/2005 | Takemoto et al. |
| 2005/0149114 A1 | 7/2005 | Cartledge et al. |
| 2005/0177176 A1 | 8/2005 | Gerbi et al. |
| 2005/0194038 A1 | 9/2005 | Brabec et al. |
| 2005/0194294 A1 | 9/2005 | Oexle et al. |
| 2005/0194312 A1 | 9/2005 | Niemeyer et al. |
| 2005/0195925 A1 | 9/2005 | Traber |
| 2005/0195944 A1 | 9/2005 | Bartels et al. |
| 2005/0196356 A1 | 9/2005 | Leinen et al. |
| 2005/0197540 A1 | 9/2005 | Liedtke |
| 2005/0197622 A1 | 9/2005 | Blumenthal et al. |
| 2005/0197684 A1 | 9/2005 | Koch |

OTHER PUBLICATIONS

Gray, H. *Anatomy of the Human Body* Clemente, C.D. ed. Williams and Wilkins Thirtieth American Edition pp: 1466-1467.

Benjamin, S.B., et al., *A Double-Blind Cross Over Study of the Garren-Edwards anti-Obesity Bubblem* Abstract Submitted to A/S/G/E/ 1987, Georgetown University Hospital and Fairfax Hospital, Washington, D.C. and Fairfax, VA.

Benjamin, S.B., *Small Bowel Obstruction and the Garren-Edwards Bubble, Lessons to be Learned?* Abstracts Submitted to A/S/G/E 1987, Division of Gastroenterology, Department of Medicine, Georgetown University Hospital, Washington, D.C.

Boyle, Thomas M., M.D., et al., *Small Intestinal Obstruction Secondary to Obturation by a Garren Gastric Bubble*, The American Journal of Gastroenterology, vol. 82, No. 1, pp. 51-53, 1987.

Büchler, M.W., M.D. et al., *A Technique For Gastroplasty As A Substitute For The Esophagus: Fundus Rotation Gastroplasty*, Journal Of The American College Of Surgeons, vol. 182, pp. 241-245, Mar. 1996.

Cass, O.W., et al., *Long-Term Follow-Up of Patients With Percutaneous Endoscopic Gastrostomy (PEG)*, Abstracts Submitted to A/S/G/E 1987, Department of Medicine, Hennepin County Medical Center, Minneapolis, MN 55415.

Chang, Craig G. M.D. [1], et al.. *Gastro-Clip® Gastroplasty: A Very Long-Term Complication*, Obesity Surgery, 14, © FD-Communications Inc,. 2004.

Clark, Charlene, R.N., *The Gastric Bubble: Medicine, Magic or Mania?* SGA Journal, vol. 9, No. 2, pp. 45-47, Fall 1986.

Cummings, David E., M.D., et al., *Plasma Ghrelin Levels After Diet-Induced Weight Loss or Gastric Bypass Surgery*, New England Journal of Medicine, vol. 346, No. 21, pp. 1623-1630, May 23, 2002.

Davenport, Horace W., Ph.D., D.Sc., *Physiology of the Digestive Tract: An Introductory Text*, 3d Ed., Cover and Table of Contents.

DeMeester, Tom T., M.D., *Evolving Concepts of Reflux: The Ups and Downs of the LES*, Canadian Journal of Gastroenterology, vol. 16, No. 5, pp. 327-331, 2002.

De Waele, B., M.D., et al., *Intragastric Balloons for Preoperative Weight Reduction*, Obesity Surgery, vpl. 10, pp. 58-60, 2000.

Edell, Steven L., et al., *Radiographic Evaluations of the Garren Gastric Bubble*, American Journal of Radiology, vol. 145, pp. 49-50, Jul. 1985.

Endo Gia* Universal, Single UseStapler and Endo GIA Roticulator*, Brochure, 8 pages, Undated.

Filipi, Charles J. M.D., et al., Transoral, *Flexible Endoscopic Suturing For Treatment OF GERD: A Multicenter Trial*, Gastrointestinal Endoscopy,. vol. 53, No. 4, pp. 416-422, 2001.

Guidant, Internet, AXIUS™ Vacuum 2 Stabilizer Systems, Internet Website—www.guidant.com/products/axius_vacuum.shtml, 8 pages, visited May 27, 2003.

Hepworth, Clive C. FRCS et al., *Mechanical Endoscopic Methods of Haemostasis For Bleeding Peptic Ulcers: A Review*, Bailliere's Clinical Gastroenterology, vol. 14, No. 3 pp. 467-476, 2000.

Ikeda, Y. et al., *New Suturing Device For Transanal Endoscopic Microsurgery*, Blackwell Science Ltd, p. 1290, 1997.

Johnson & Johnson Gateway[SM] Endopath 3mm, 5mm and 10 mm Diameter Endoscopic Instruments, Internet Website—www.inigateway.com/home.ihtml?loc=USENG&page=viewContent&parentld-0900. . . , 3 pages, visited May 29, 2003.

Kirby, Donald F., *Incomplete Small Bowel Obstruction by the Garren-Edwards Gastric Bubble Necessitating Surgical Intervention*, The American Journal of Gastroenterology, vol. 82, No. 3, pp. 251-253, 1987.

Nieben, Ole Gyring, et al., *Intragastric Balloon as an Artificial Bezoar for Treatment of Obesity*, The Lancet, pp. 198-199, Jan. 23, 1982.

Percival, Walter L., M.D., *"The Balloon Diet": A Noninvasive Treatment for Morbid Obesity. Preliminary Report of 1908 Patients*, The Canadian Journal of Surgery, vol. 27, No. 2, pp. 135-136.

Power Medical Interventions Digital and Wireless Medical Technology, Product Innovation: SurgASSIST™ Internet Website—www./pmi2.com/access_flexibility.asp, 6 pages, visited May 29, 2003.

Snowden Pencer, Diamon-Flex Angled Snake Retractor (class 1, 878.4800), Appendix F.f, Undated.

Stoltenberg, P.H., et al., *Intragastric Balloon Therapy of Obesity: A Randomized Double-Blind Trial*, Abstracts of Papers 1985, Scott & White Clinic, Texas A&M College of Medicine, Temple, Texas.

Swain, C. Paul, M.D. et al., *An Endoscopic Sewing Machine*, Gastrointestinal Edoscopy, vol. 32, No. 1 pp. 36-38 1986.

Swain, C. Paul, M.D., *Endoscopic Sewing And Stapling Machines*, Endoscopy pp. 205-210, © Georg Thieme Verlag Stuttgart, New York, 1997.

Swain, C. Paul, M.D. et al., *An Endoscopic Stapling Device: The Development Of A New Flexible Endoscopically Controlled Device For Placing Multiple Transmural Staples In Gastrointestinal Tissue*, Gastrointestinal Endoscopy, vol. 35, No. 4, pp. 338-339, 1989.

Swain, C. Paul, M.D., *Endoscopic Suturing*, Bailliere's Clinical Gastroenterology, Bailliere's Tindall,, vol. 13, No. 1, pp. 97-108, 1999.

Taylor, T. Vincent, et al., *Gastric Balloons for Obesity*, The Lancet, Abstract, Mar. 27, 1982.

Vandenplas, Y., et al., *Intragastric Balloons in Adolescents With Morbid Obesity*, European Journal of Gastroenterology & Hepatology, vol. 11, No. 3, pp. 243-245, 1999.

Villar, Hugo V., M.D., et al., *Mechanisms of Satiety and Gastric Emptying After Gastric Partitioning and Bypass*, Surgery, pp. 229-236, Aug. 1981.

Wullstein, C., et al., *Compression Anastomosis (AKA-2) in Colorectal Surgery: Results in 442 Consecutive Patients*, British Journal of Surgery 2000, pp. 1071-1075.

* cited by examiner

MAGNETIC ANCHORING DEVICES

CROSS-REFERENCE TO RELATED APPLICATIONS

This application is a continuation of U.S. patent application Ser. No. 10/288,820 filed Nov. 5, 2002, now U.S. Pat. No. 6,656,194 which is hereby incorporated by reference in its entirety.

FIELD OF THE INVENTION

The present invention relates generally to medical devices and methods. More particularly, the present invention relates to devices and methods for the magnetic attachment of expandable devices and the like within a patient's body cavity, such as the stomach, intestine or gastrointestinal tract.

BACKGROUND OF THE INVENTION

In cases of severe obesity, patients may undergo several types of surgery either to tie off or staple portions of the large or small intestine or stomach, and/or to bypass portions of the same to reduce the amount of food desired by the patient, and the amount absorbed by the intestinal tract. Procedures such as laparoscopic banding, where a device is used to "tie off" or constrict a portion of the stomach, or placement of intragastric balloons, can achieve these results.

Endoscopic procedures that have been used to assist weight loss have primarily focused on placement of a balloon or other space-occupying device in the patient's stomach. This fills portions of the stomach and provides the patient with a feeling of fullness, thereby reducing food intake. To accomplish these procedures, an endoscope is utilized to guide the balloon through the patient's mouth and down the esophagus to the stomach. Usually these procedures have allowed placement of the device for 3-6 months, and are coupled with counseling and other types of behavioral modification programs.

Many of the conventional surgical interventions require the patient to submit to an intervention under general anesthesia, and can require large incisions and lengthy recovery time. The less invasive procedures, although clinically efficacious in many cases, suffer from complications ranging from deflation of the devices to insufficient anchoring of these devices resulting in unsustained weight loss, stomach erosion, bowel obstruction and even death.

Many of these devices are neither robust enough nor are they adequately secured within the stomach to sustain long term implantation. As a result, many implanted devices are implanted in such a manner as to remain unattached or free-floating within the stomach. Further, due to the caustic nature of stomach acids and other factors, many of the implants deflate and migrate into the intestine, causing bowel obstructions and in some cases death. Also, many devices are not well designed for removal, leading to additional technical difficulties for the clinician.

BRIEF SUMMARY OF THE INVENTION

The present invention provides improved methods and apparatus for implanting and anchoring space-occupying devices into the gastrointestinal system of a patient, e.g., the stomach of the patient, which can be deployed in a minimally invasive manner such as transesophageal endoscopy. The invention allows greater access to procedures and devices by patients who might not otherwise be treated surgically as "morbidly obese" (at or above a Body Mass Index (BMI) of 40 kg/m3), but who may just be moderately obese or overweight (BMI of between 25 to 40 kg/m3). In addition, patients who require more invasive surgery for an unrelated ailment, may need a minimally invasive way to lose the weight prior to their more invasive procedure, thereby reducing the risks associated with general anesthesia, or otherwise enabling the more invasive procedure.

Expandable devices that may be inserted into the stomach of a patient may be maintained within the stomach by anchoring or otherwise fixing the device to the stomach wall of the patient. Such expandable devices, e.g., an inflatable balloon, may comprise two portions, an inner portion and an outer portion, the inner portion being able to maintain its shape, regardless of the integrity of the outer portion. Other expandable balloon devices may be used to maintain their expanded shape and desired volume, independent of any small leaks that may develop over time, or they may be configured to maintain a volume of the space-occupying device that can be adjusted in-situ, to change the size of the device after implantation.

The space-occupying devices may be anchored to the stomach wall by an anchoring device that may comprise one or more proximal magnetic devices for magnetically coupling with a distal magnetic anchor located on the stomach wall. The magnetic device and anchor may both be magnets or portions of magnetizable material. Similarly, the proximal magnetic device may be a magnet or portion of magnetizable material while the distal magnetic anchor may be a magnet of opposite polarity, or a magnetically attractive metal. Alternatively, the proximal device may be a magnetically attractive metal and the distal anchor may be a magnet.

The magnetic device may be affixed to the space-occupying member, or may be movable within the member and directable to the site of attachment at the stomach wall by magnetic attraction. The magnetic device may be completely within the space-occupying member. On the other hand, the magnetic device may be positioned on an external surface of the space-occupying member or be integral thereto, and be configured such that a portion of it extends at least partially through one or several folds of the patient's stomach wall, thereby maintaining the device within the patient's stomach.

As will soon become apparent, the magnetic device and anchor may take any variety of configurations and be made of any number of materials. Similarly, the device and anchor may have a variety of different surfaces. They may be textured, or have a detent. In this way, adequate perfusion of tissue is accomplished and ischemic tissue necrosis is prevented. Any number of coupling devices may be used.

DETAILED DESCRIPTION OF THE INVENTION

Figure 1:
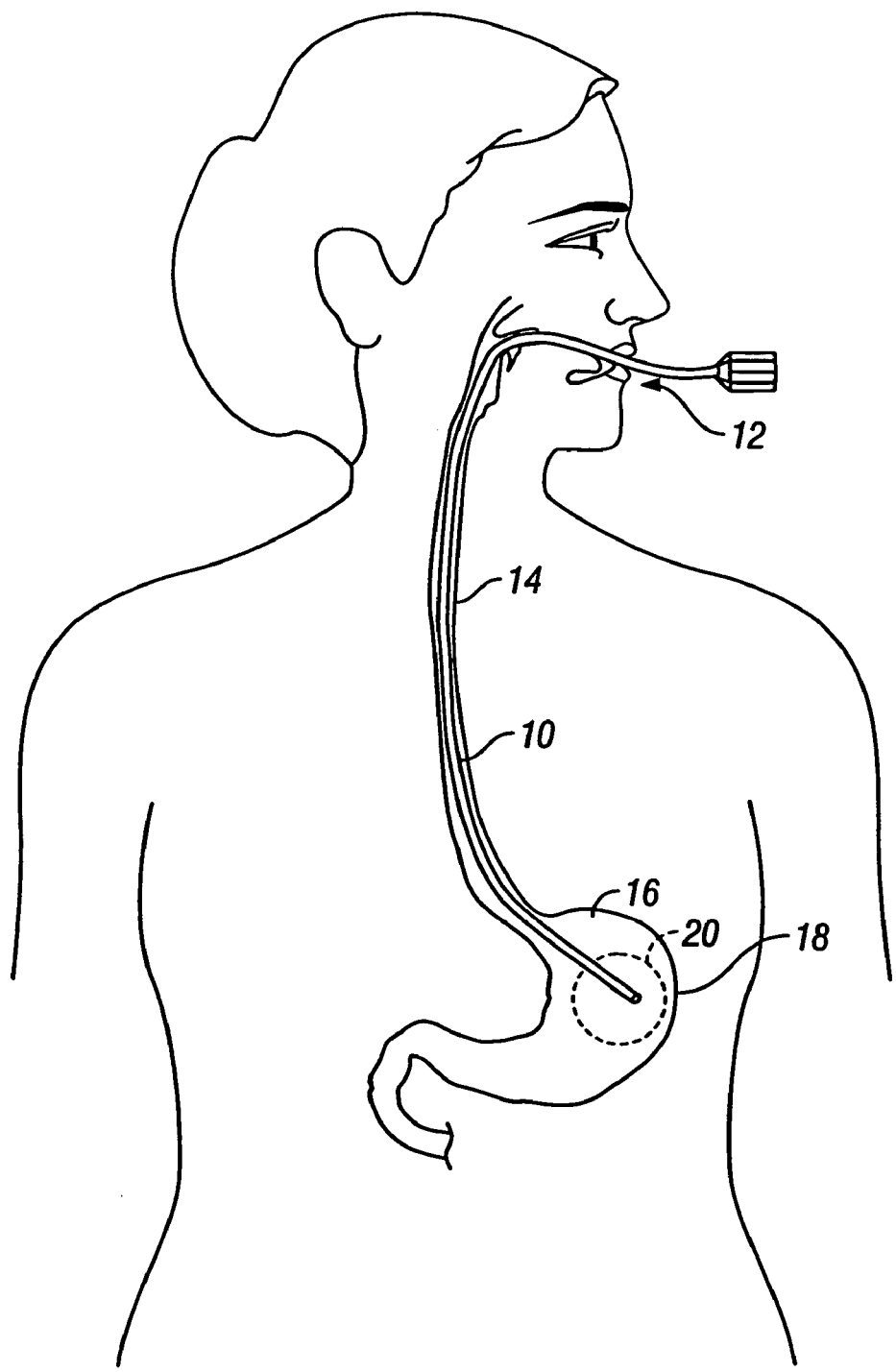
FIG. 1 shows a schematic illustration of a delivery endoscope advanced to a region of interest within the stomach of a patient.

Expandable devices may be inserted into the stomach of a patient and be attached to the stomach walls by magnetic anchoring devices. Although the magnetic anchoring devices disclosed herein describe attachment to the stomach walls, the anchors may be utilized in any hollow body organ or interior body space for temporarily or permanently anchoring expandable devices to tissue. The description herein of use of the magnetic coupling device with a stomach wall is merely illustrative. FIG. 1 illustrates a delivery endoscope 10 that may be used to deliver the expandable devices into, e.g., stomach 18 of a patient. Endoscope 10 is shown as having been advanced through the mouth 12 and esophagus 14 of the patient to position the distal end of endoscope 10 within a region of interest 20 within stomach 16.

Figure 2A:
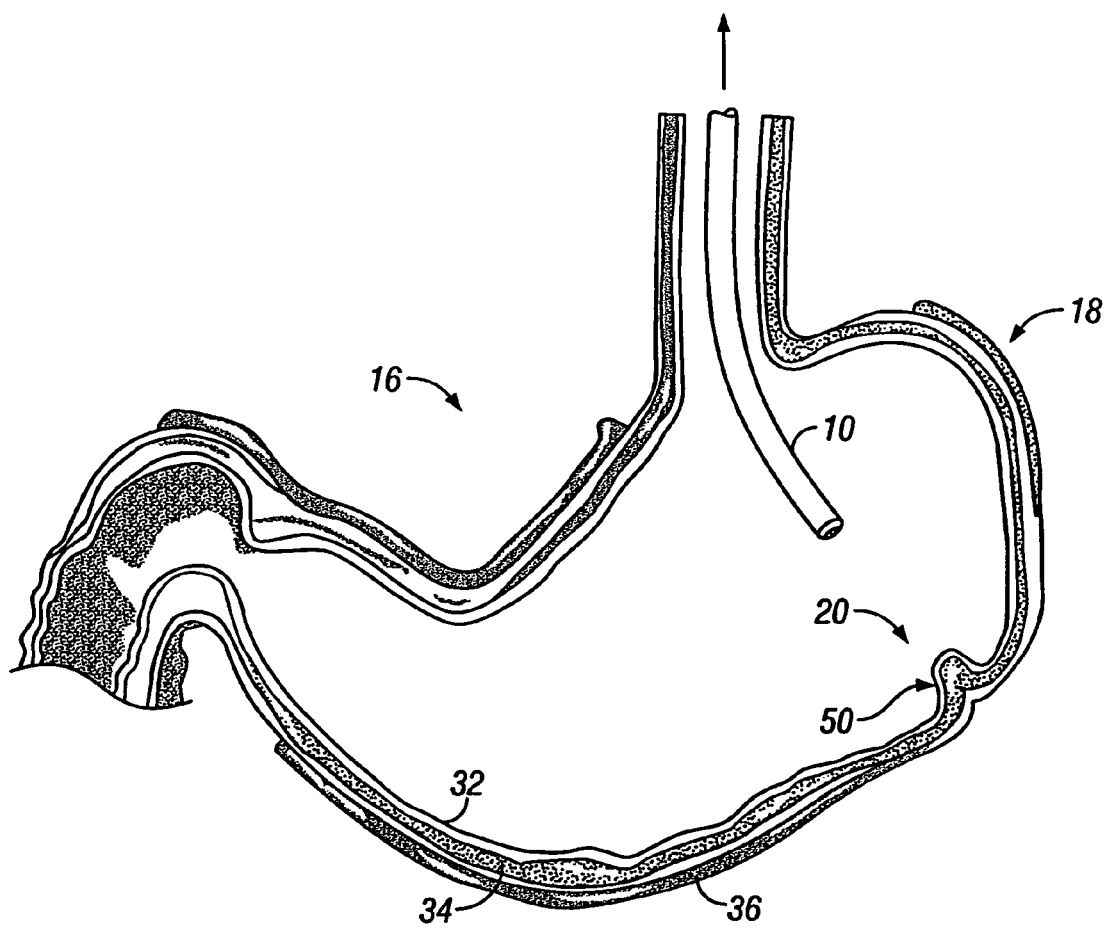
FIG. 2A shows a cross-sectional view of a stomach within which a tissue fold has been formed from the walls of the stomach.

FIG. 2A shows a cross-sectional view of stomach 16 within which endoscope 10 has been positioned adjacent to the region of interest 20. Any number of conventional tools may be passed through the working channel of endoscope 10, or any of the tissue acquisition devices as described in further detail in U.S. patent application Ser. No. 09/871,297 filed May 30, 2001 or U.S. patent application Ser. No. 10/188,547 filed Jul. 2, 2002, both of which are commonly owned and are incorporated herein by reference in their entirety.

Figure 2B:
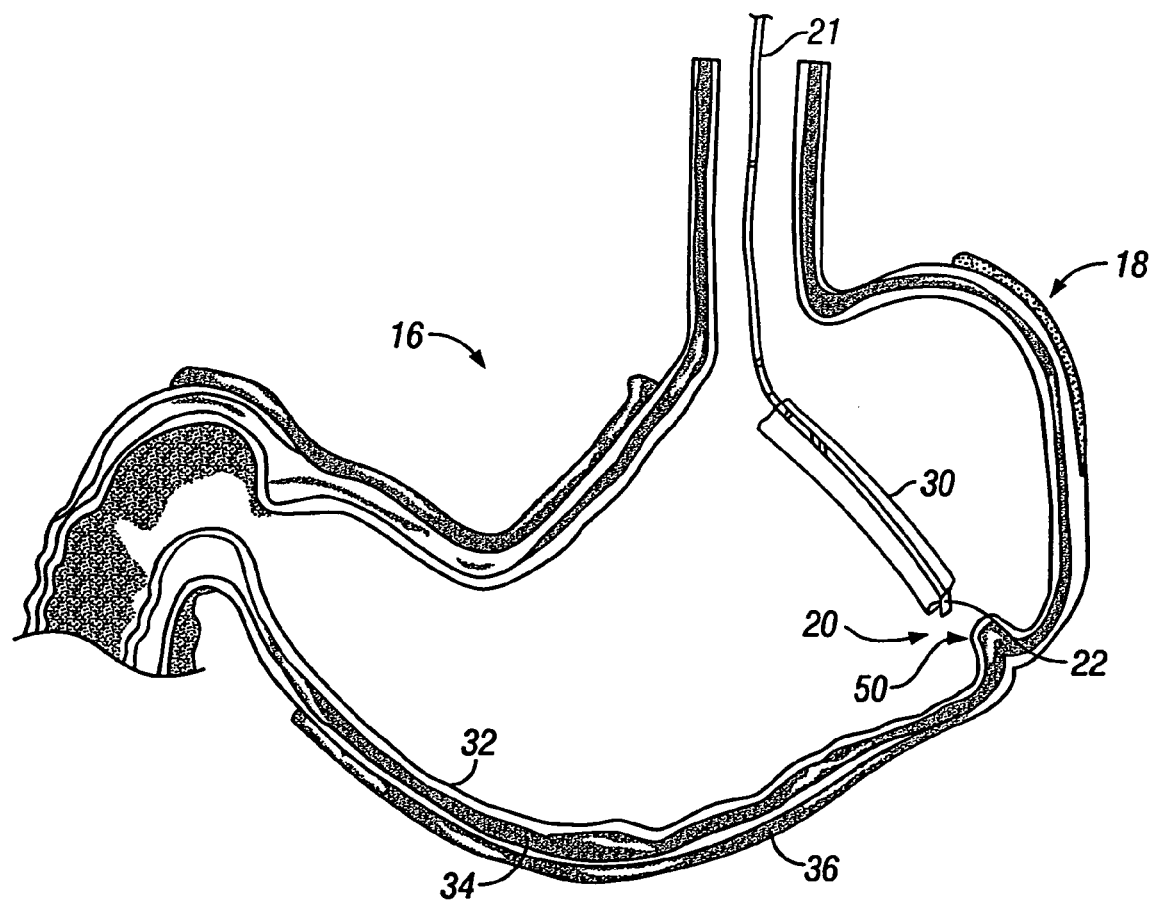
FIG. 2B shows the stomach of FIG. 2A in which an inflatable or space-occupying member (in its deflated or unexpanded state) has been advanced for anchoring to the tissue fold.

The space occupying device, e.g., an expandable scaffold, an inflatable balloon, etc., may be advanced within stomach 16 towards the region of interest 20 for anchoring to the stomach wall. As shown in FIG. 2B, space-occupying member 30 may be advanced using an elongate delivery member 21, e.g., endoscope 10 or any one of the delivery devices as shown and described in U.S. patent application Ser. No. 09/816,850 filed Mar. 23, 2001, which is commonly owned and is incorporated herein by reference in its entirety. The use of an inflatable balloon in these examples is intended to be illustrative and any number of space-occupying devices, such as an expandable scaffold, may be utilized as described in the incorporated application.

Figure 3:
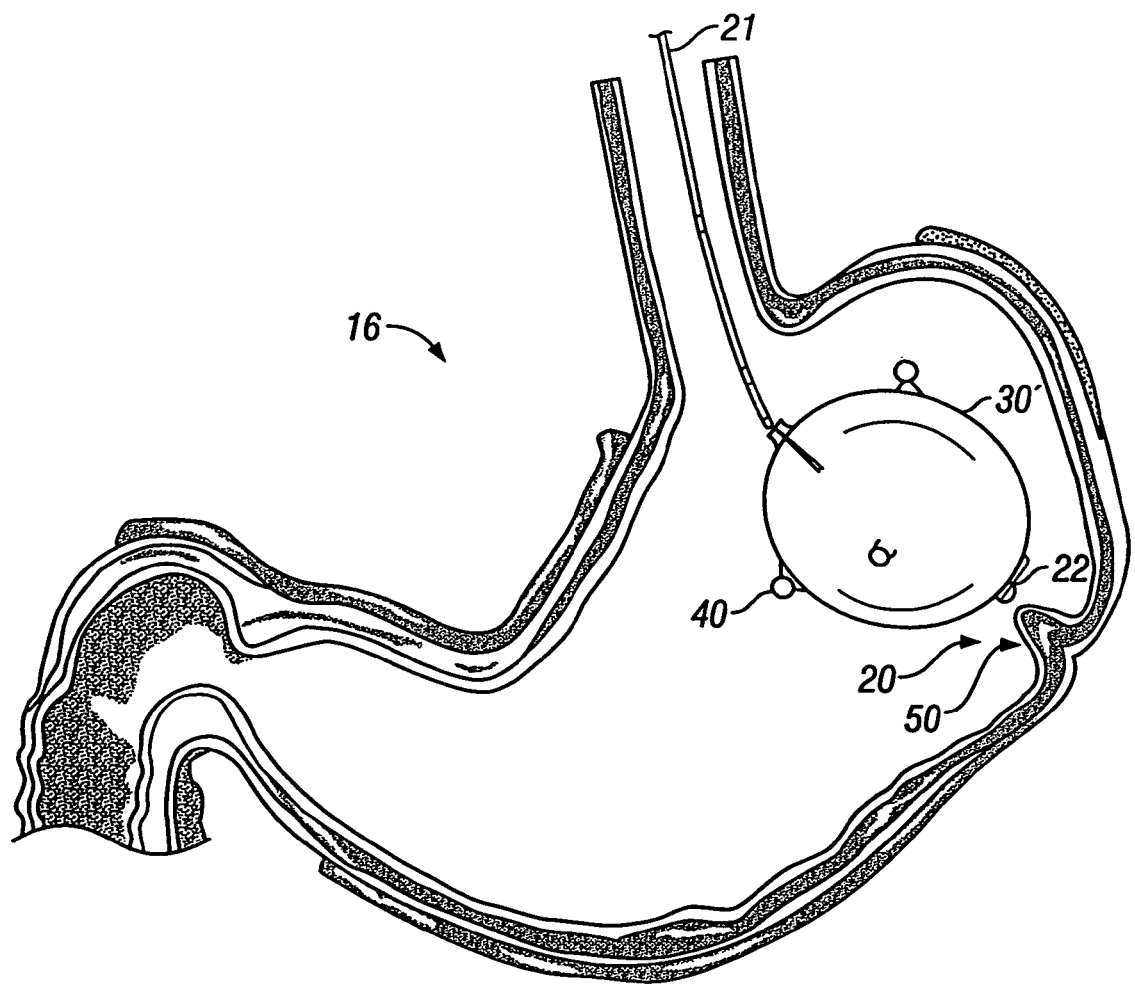
FIG. 3 shows the stomach of FIGS. 2A and 2B in which the space-occupying member has been expanded for deployment.

As seen in FIG. 3, delivery member 21 may be used to inflate space-occupying member 30 into its expanded shape 30'. The surface of space-occupying member 30' may have one or several tabs 40 extending from or defined along its outer surface to allow a grasping tool to manipulate or remove space-occupying member 30' during the procedure or post-procedurally.

Space-occupying member 30 may be formed of a urethane interior and a silicone exterior. The urethane provides durability to the balloon for resisting undesirable rupture or leakage and the silicone exterior provides for smoothness and conformability, to avoid unnecessary trauma or irritation to the stomach lining. In another variation, the member 30 is formed of a composite of silicone, aluminized polyester film, and polyethylene. In this variation, the space occupying device is formed by heat-sealing sheets of mylar/polyethylene composite. The seam is then trimmed to a minimum size and a valve attached. The assembly is then dipped in room temperature vulcanizing (RTV) liquid silicone which, once cured, will leave a smooth surface, which may or may not have a palpable seam. Alternatively, the space-occupying device can be rotated as the silicone cures, to allow for a more consistent coating to form.

A variety of sizes and shapes of space-occupying member 30 are contemplated, and it is to be appreciated that one skilled in the art would be competent to choose a particular shape and size according to the particular application. The space-occupying member 30 can be, for example, a spherical or ellipsoidal balloon or another suitable shape. In the case of an ellipsoidal balloon, one method of anchoring such a balloon is along the longer axis of the balloon; however, anchoring may also be achieved by anchoring along the shorter axis of the balloon. Balloon volumes can vary, but a typical volume is approximately 500 cubic centimeters (cc).

Figure 4A:
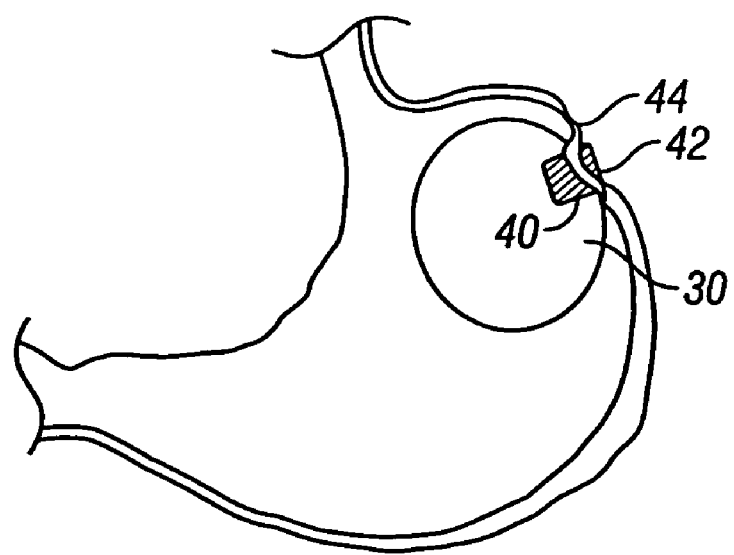
FIG. 4A shows one variation of the space-occupying member where the magnetic device is affixed thereto and is magnetically coupled to the magnetic anchor on the stomach wall.

One variation of space-occupying member 30 is shown in FIG. 4A. In this variation, the space-occupying member comprises at least one proximal magnetic device 40 for magnetically coupling with a distal magnetic anchor 42 affixed to the stomach wall 44. The magnetic device and anchor may be magnets or portions of a magnetizable material. Similarly, the proximal magnetic device may be a magnet or portion of magnetizable material while the distal magnetic anchor may be a magnet of opposite polarity, or a magnetically attractive metal. Alternatively, the proximal device may be a magnetically attractive metal and the distal anchor may be a magnet.

The magnetic device and anchor should be resilient and provide strong enough magnetic forces, approximately ½ lbf to 2 lbf, to result in magnetic coupling across the stomach wall, but not be so strong as to traumatize the surrounding tissue, cause ischemia, or pressure necrosis. The attachment of the space-occupying member to the stomach wall may be accomplished prior to, during, or even after inflation or expansion of member 30 and may be done by any number of manipulation tools endoscopically or laparoscopically delivered and positioned, as appreciated by one skilled in the art.

Figure 4B:
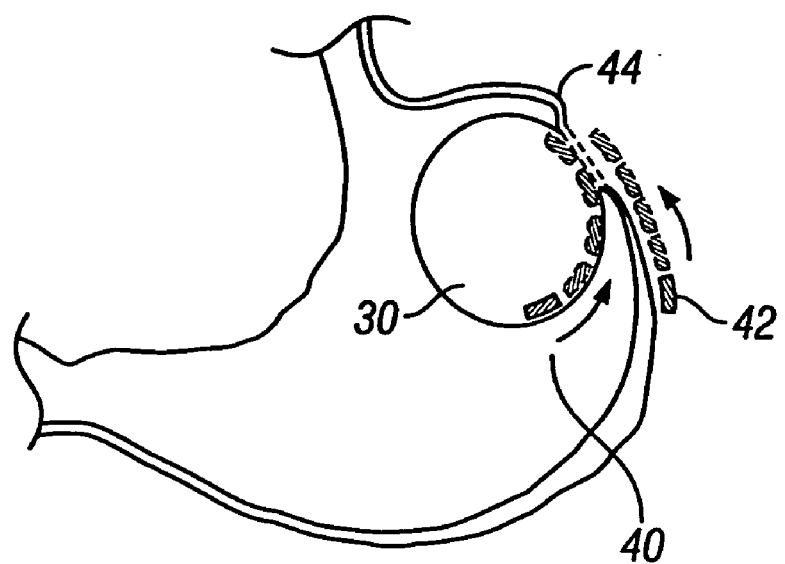
FIG. 4B shows another variation of the space-occupying member where the magnetic device is un-affixed thereto and is movable to the site of attachment with the magnetic anchor on the stomach wall.

The magnetic device of the space-occupying member may or may not be affixed thereon. For example, as shown in FIG. 4B, the magnetic device 40 may be non-affixed and be movable to the site of attachment just prior to attachment. This may be accomplished by using the magnetic anchor 42 to be affixed to the stomach wall 44 to attract mobile magnetic device 40 and pull it to the site of attachment. Movement of the mobile magnetic device 40 may also be accomplished by any other similar magnetic attraction means.

Figure 5A:
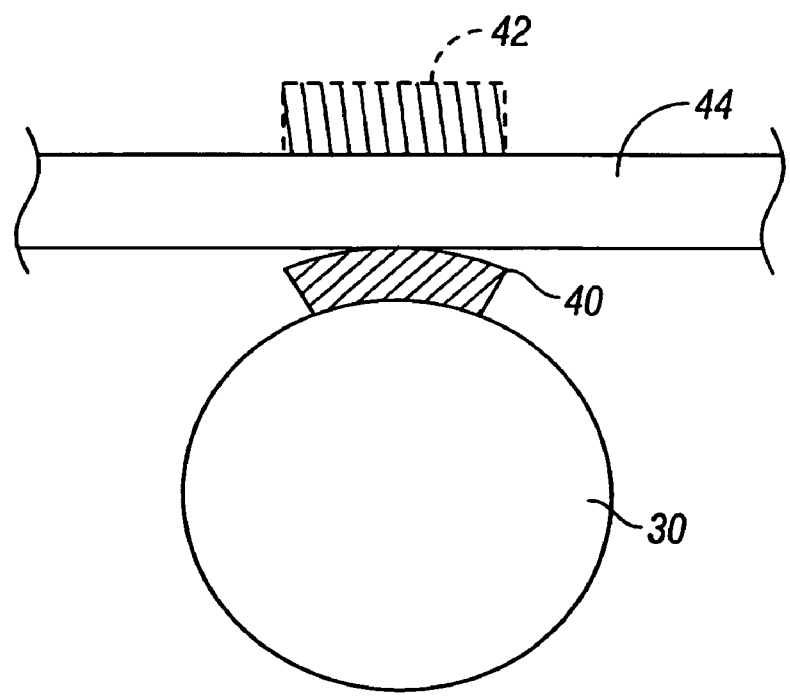
FIG. 5A shows one variation where the magnetic device of the present invention is positioned on an external surface of the space-occupying member.
Figure 5B:
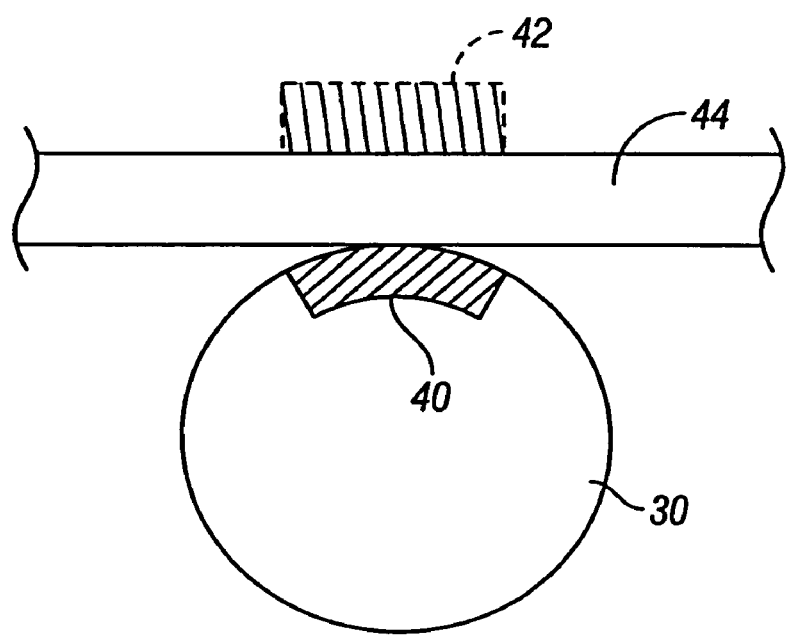
FIG. 5B shows another variation where the magnetic device of the present invention is positioned on an internal surface of the space-occupying member.
Figure 5C:
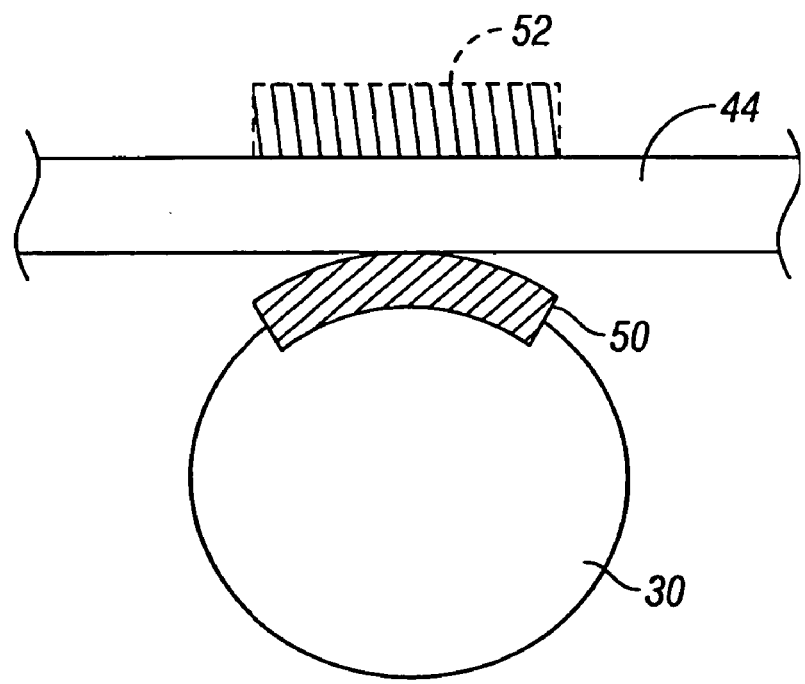
FIG. 5C shows yet another variation where the space-occupying member comprises an integral magnetic device.
Figure 5D:
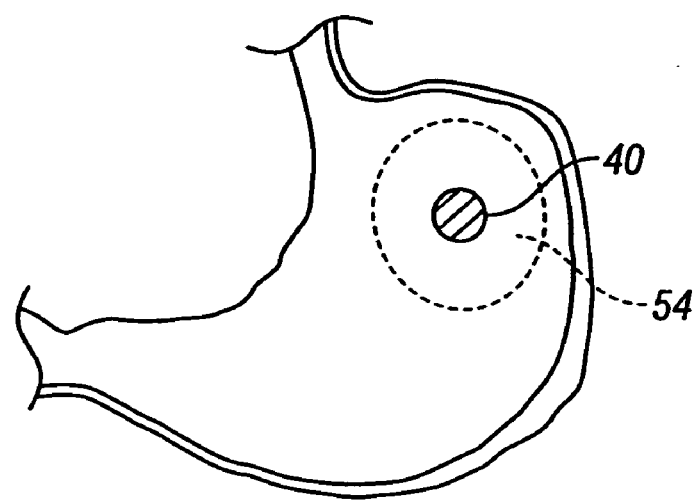
FIGS. 5D through 5H show variations of the present invention in which the magnetic device is used with a toroidal space-occupying member.
Figure 5E:
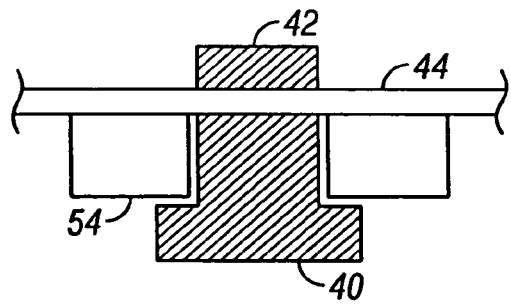
Figure 5F:
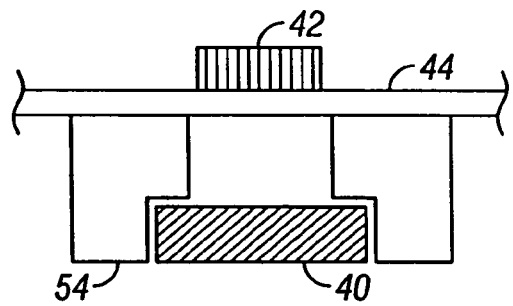
Figure 5G:
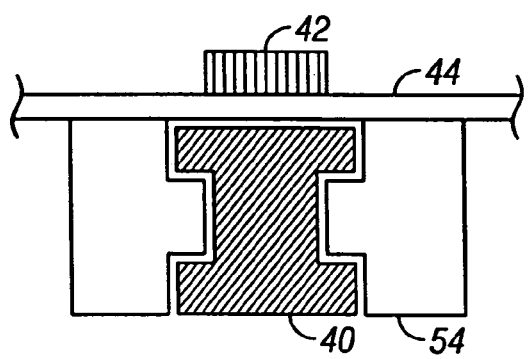
Figure 5H:
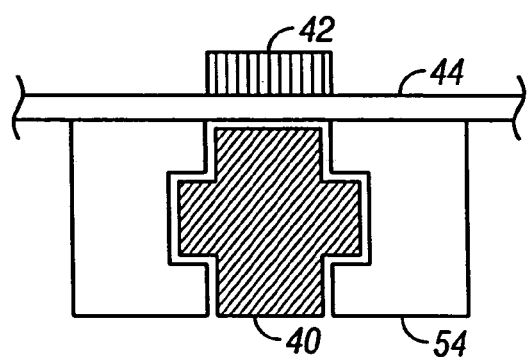

The magnetic device may be positioned on an external surface of the space-occupying member or may be positioned on its internal surface as shown in FIGS. 5A and 5B respectively. In one variation, shown in FIG. 5C, the space-occupying member itself comprises integral magnetic device 50, having an external magnetic, magnetizable or metallic surface 52. In another variation, shown in FIGS. 5D through 5H, the magnetic device and anchor of the present invention are used in combination with a toroidal space-occupying member. FIG. 5D illustrates toroidal space-occupying member 54 positioned within a stomach, and magnetic device 40 positioned within an opening of the toroidal space-occupying member 54. The toroidal space-occupying member may have any number of configurations and the magnetic device may have any number of corresponding configurations, adaptable to the opening of the toroidal space-occupying member. For example, toroidal space-occupying member 54 may a uniform inner circular circumference, or may instead, have a non-uniform inner circumference. A few illustrative variations are provided in FIGS. 5E through 5H. The magnetic devices may be extremely flexible or rigid, or have any tensile strength therebetween.

The magnetic anchor of the stomach wall may be made of a biocompatible material or be coated with a material, eg. silicone, to achieve biocompatability. Similarly, when the magnetic device is external or integral to the space-occupying member, as shown in FIGS. 5A and 5D respectively, any surface exposed to the body should be made biocompatible.

Several methods may be used to secure or place the magnetic anchor on a surface on the stomach wall. For example, portions of the stomach are accessible via minimally invasive surgery. The stomach may be accessed via the abdominal wall, under the lower ribs on the left side, or under the left lobe of the liver. Any of these access sites may be selected depending on the desired placement of the magnetic anchor.

One method of attaching the magnetic anchor to the stomach wall is laparoscopically. Using this method, a thin, telescope-like instrument (e.g., a laparoscope) is inserted through a small incision at the umbilicus (belly button). The laparoscope is connected to (or comprises) a tiny video camera, which projects a view of the abdomen onto a video monitor located in the operating room. Sometimes the abdomen is inflated with a gas (e.g., carbon dioxide).

Several additional small incisions (e.g., four to five depending on the particular surgical needs) are then made near the site of the laparoscope. Through these incisions, the surgeon may insert instruments for maneuvering the magnetic anchor and suturing it to the stomach wall. Similarly, any other instruments necessary for facilitating the attachment of the magnetic anchor to the stomach wall may be inserted through these incisions. After the magnetic anchor is attached to the stomach wall, the small incisions are closed with sutures and covered with a protective bandage.

Another method of attaching the magnetic anchor to the stomach wall makes use of small incisions, without using the laparoscopic method. Simple incisions may be made while the patient is under local anesthesia for accessing the stomach wall and for affixing the magnetic anchor thereto. If the patient prefers, general anesthesia may be administered. However because the incisions will be small (not the 8–10 inch incisions typically performed in most "open" surgeries), recovery time and scarring will be minimal.

For example, a small incision may be made in the linea alba by a downward cut from the ensiform cartilage. The peritoneal cavity may then be opened. The stomach is now accessible for affixing the magnetic anchor. The anchor itself may comprise a portion to allow for suturing to the stomach wall, or may have an aperture for suturing therethrough. Any number of anchor configurations may be selected. Once the anchor configuration has been selected, the method of physically securing it to the stomach wall will become readily apparent to those skilled in the art. Of course, if the laparoscopic or simple incision methods prove unsuccessful during surgery itself, the traditional "open surgery" method may be used to attach the magnetic anchor to the stomach wall.

Similarly, any number of methods may be used to affix the magnetic device to the space-occupying member when it is desirable to have the device affixed thereto. The appropriate securing method may depend on the material comprising the space-occupying member and on whether the device is to be affixed to an external or internal surface. This is because the body may be unable to break down certain substances and their introduction into the body may pose serious health risks. However, when the device is to be affixed to an internal surface of the space-occupying member, a variety of different adhesives, glues, cements, resins, bonding agents, or other methods may be used. However, special care must be taken to select a securing agent that is non-corrosive and that will not degrade or permeate the space-occupying member.

Figure 6A:
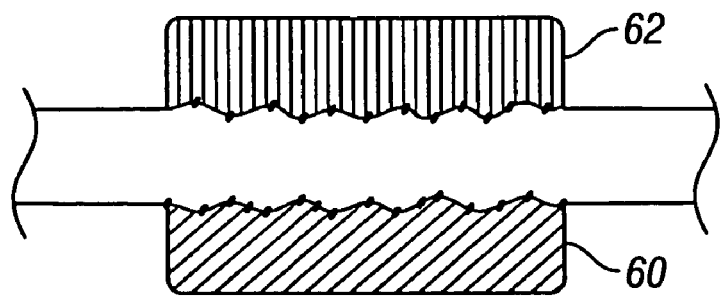
FIG. 6A shows one variation where the surfaces of the magnetic device and anchor are textured.
Figure 6B:
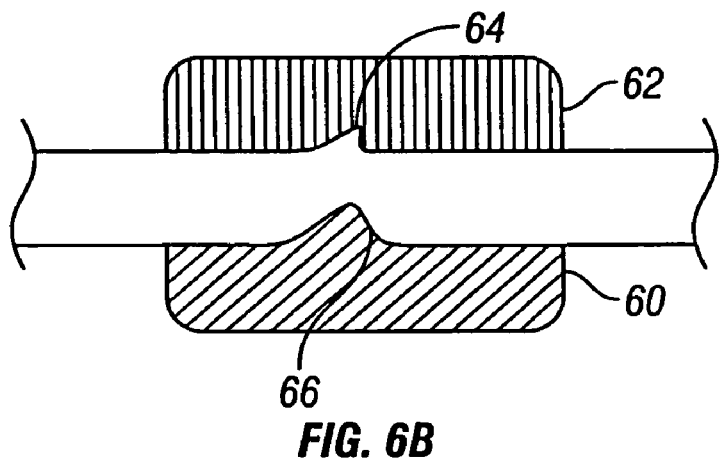
FIG. 6B shows another variation where the magnetic anchor comprises at least one detent for receiving at least one protruding portion of the magnetic device.
Figure 6C:
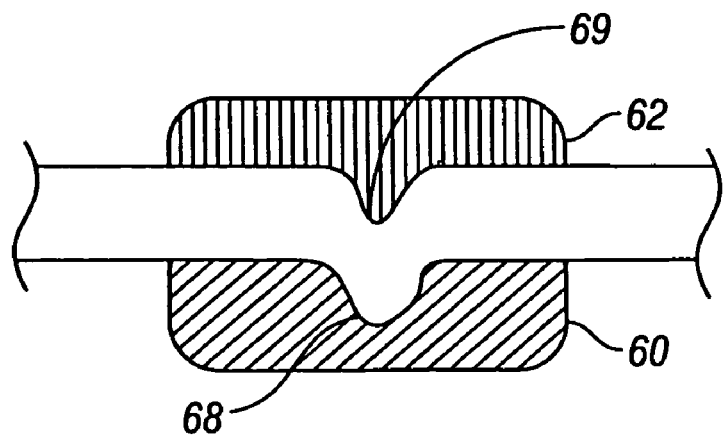
FIG. 6C shows another variation where the magnetic device comprises at least one detent for receiving at least one protruding portion of the magnetic anchor.

FIG. 6A shows one variation where the proximal magnetic device 60 and distal magnetic anchor 62 have textured surfaces. This may help facilitate coupling and also help prevent slippage of the space-occupying member. In addition, having a texture or tread allows for adequate perfusion of the tissue and helps prevent ischemic tissue necrosis. Similarly, the magnetic device or anchor may comprise at least one detent for receiving at least one protruding portion of the corresponding device or anchor as shown in FIGS. 6B and 6C. In FIG. 6B, distal magnetic anchor 62 has detent 64 for receiving protruding portion 66 of proximal magnetic device 60. Similarly, in FIG. 6C, proximal magnetic device 60 has detent 68 for receiving protruding portion 69 of distal magnetic anchor 62.

In another variation a tissue fold may be utilized. As illustrated in FIG. 2, the tissue layers of stomach 16 are comprised of the mucosal layer 32, the muscularis or fibrous muscular layer 34, and the serosal layer 36. In forming tissue fold 50, at least two layers of stomach tissue are folded to contact itself such that a certain amount of fibrous tissue overlap occurs prior to fastening tissue fold 50 in a configuration akin to a lap joint. The amount of the overlap can vary and needs only be sufficient enough to result in joining of the fastened sections, thereby creating a tissue bridge along the length of the fastened tissue. Formation of tissue folds was described in detail in U.S. patent application Ser. No. 10/215,070 filed on Aug. 7, 2002 which is commonly owned and incorporated herein by reference in its entirety.

Figure 7A:
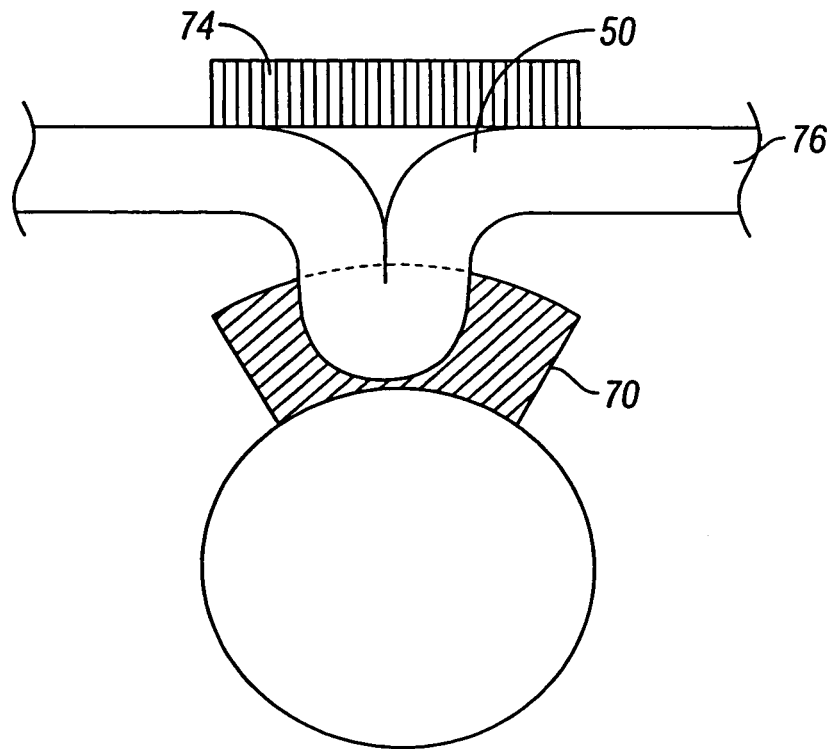
FIG. 7A shows how a portion of the magnetic device may be positioned through a tissue fold when the magnetic device is on an external surface of the space-occupying member.
Figure 7B:
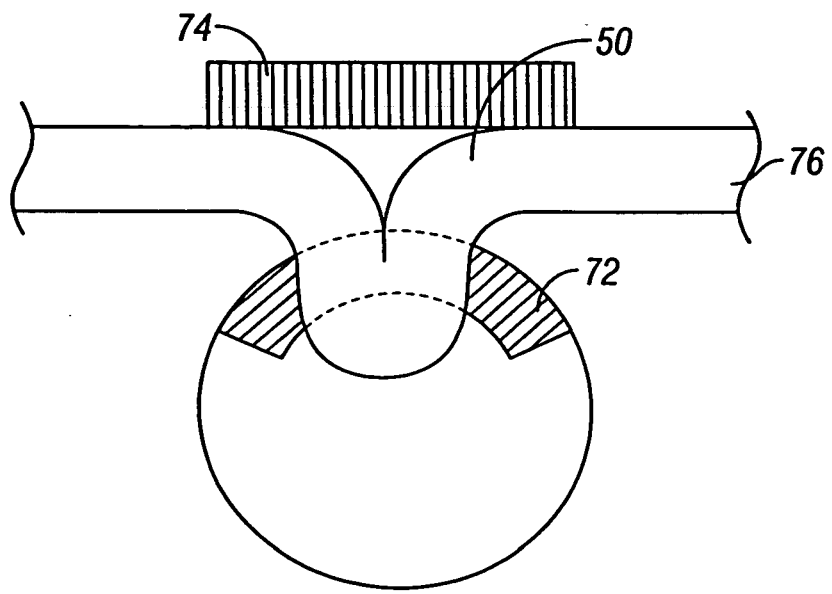
FIG. 7B shows how a portion of the magnetic device may be positioned through a tissue fold when the space-occupying member comprises an integral magnetic device.

The tissue bridge may be formed of various layers of the stomach and may include scar tissue and other elements of effective wound healing. Once tissue fold 50 has been desirably configured, a portion of the magnetic device may be positioned therethrough for maintaining the tissue fold configuration. For example, as shown in FIGS. 7A and 7B, when the magnetic device is on the external surface of space-occupying member 70 or integral thereto 72, a portion of it may be inserted through the tissue fold. Magnetic anchor 74 on stomach wall 76 is then positioned on a corresponding surface distal thereto for coupling with the magnetic device.

Any number of such tissue folds as practicable may be used depending upon the desired results and anchoring configuration. Similarly, any number of magnetic coupling devices may be used. For example, in some instances it may be desirable to magnetically couple the space-occupying member to the stomach wall at more than one point of attachment. This may provide extra stability to the space-occupying member and also help prevent its migration or detachment in the event that one set of magnetic coupling device and anchor becomes loose. In this way, the prior art problems of inadequately secured devices may further be reduced or eliminated.

Although illustrative variations of the present invention are described above, it will be evident to one skilled in the art that various changes and modifications may be made without departing from the invention. For instance, variations of the present invention may be used as permanent or temporary anchoring devices. Moreover, modified variations may also be used in other regions of the body, e.g., for use in the intestinal tract, etc. It is intended in the following claims to cover all such changes and modifications that fall within the true spirit and scope of the invention.

The invention claimed is:

1. A method for attaching a magnetic anchor to a stomach wall comprising:

accessing at least a portion of a stomach wall and forming a tissue fold;

attaching a first magnetic anchor to the tissue fold on the interior of the stomach wall; and attaching a second magnetic anchor to the tissue fold on the exterior of the stomach wall, wherein the second magnetic anchor is attracted to the first magnetic anchor.

2. The method of claim 1 wherein the step of attaching the magnetic anchor comprises suturing the second magnetic anchor to the tissue fold of the stomach wall.

3. The method of claim 2 wherein the second magnetic anchor is configured to allow suturing of the second magnetic anchor to the tissue fold of the stomach wall.

4. The method of claim 3 wherein the second magnetic anchor defines an aperture.

5. The method of claim 3 wherein the second magnetic anchor has a portion to allow for suturing of the second magnetic anchor to at least a portion of the stomach wall.

6. The method of claim 1 wherein the step of accessing a portion of the stomach wall comprises making at least one small incision in a linea alba.

7. The method of claim 6 wherein the at least one small incision is less than eight inches in length.

8. The method of claim 1 wherein the step of accessing a portion of the stomach wall comprises laparoscopically accessing the portion.

9. The method of claim 1 wherein the step of accessing a portion of the stomach wall comprises making at least one incision in a linea alba, wherein the incision is greater than eight inches in length.

* * * * *